ated Cellular Biology 4, 1134-1140, Jun. 1984.
United States Patent [19]

Furuichi et al.

[11] Patent Number: 4,764,460

[45] Date of Patent: Aug. 16, 1988

[54] RECOMBINANT SIGMA NS PROTEIN

[75] Inventors: Yasuhiro Furuichi, Kamakura; Michael A. Richardson, Yokohama, both of Japan

[73] Assignee: Hoffmann-La Roche Inc., Nutley, N.J.

[21] Appl. No.: 796,372

[22] Filed: Nov. 8, 1985

[51] Int. Cl.⁴ .................... C12Q 1/68; G01N 33/566; C12N 15/00
[52] U.S. Cl. .................................. 435/6; 435/172.3; 435/948; 436/501; 935/77; 935/78
[58] Field of Search ...................... 435/6, 5, 29, 172.1, 435/172.3, 235, 236, 239; 436/63; 935/11, 19, 77, 78

[56] References Cited

U.S. PATENT DOCUMENTS 4,358,535 11/1982 Falkow et al. .................... 435/5

OTHER PUBLICATIONS

Lin et al., J. Virol., 55:2, pp. 509-512 (1985).
Thomas, P. S., PNAS, 77:9, pp. 5201-5205 (1980).
"Complete Nucleotide Sequence of the mRNA Coding for the N Protein of Vesicular Stomatitis Virus (New Jersey Serotype)".
Amiya K. Banerjee, Dennis P. Rhodes, and Dalip S. Gill Virology 137, 432-438, 84 "Expression of Enzymatically Active Reverse Transcriptase in *Escherichia coli*".
Naoko Tanese, Monica Roth, and Stephen P. Goff Proc. Natl. Adac. USA 82 4944-4948 85 "Specific Interactions of Vesicular Stomatitis Virus L and NS Proteins with Heterologous Genome Ribonucleo-Protein Template Lead to mRNA Synthesis In Vitro".
Bishnu P. De and Amiya K. Banerjee Journal of Virology 51, 628-634, Sep. 1984.
"La Antigen Recognizes and Binds to the 3'-Oligouridylate Tail of a Small RNA", Michael B. Mathews and A. Michele Francoeur Molecular and Cellular Biology 4, 1134-1140, Jun. 1984.
"Sequence of the Viral Replicase Gene from Foot-and-Mouth Disease Virus C₁-Santa Pau (C-S8)".
Encarnacion Martinez-Salas, Juan Ortin and Esteban Domingo Gene 35, 55-61, 1985, "Expression of a Functional Influenza Viral Cap-Recognizing Protein by using a Bovine Papilloma Virus Vetor".
Janet Braam-Markson, Carol Jaudon, and Robert M. Krug Proc. Natl. Acad. Sci. USA 82, 4326-4330, Jul. 1985.
Huismans, J. and Joklik, W., "Reovirus Coded Polypeptides in Infected Cells: Isolation of Two Native Monomeric Polypeptides with Affinity for Single-Stranded and Double-Stranded RNA, Respectively," *Virology*, 70, 411-424, 1976.

*Primary Examiner*—Sidney Marantz
*Assistant Examiner*—Janelle Graeter
*Attorney, Agent, or Firm*—Jon S. Saxe; George M. Gould; Norman C. Dulak

[57] ABSTRACT

This disclosure relates to the synthesis by application of recombinant DNA technology of recombinant reovirus nonstructural protein sigma NS and its use as a nonspecific binding agent for single stranded (ss) RNA's. This property of sigma NS protein can be employed when it is used as a reagent in protecting unstable RNA during extraction processes and more significantly as a reagent for the concentration of (ss) RNA samples for use in hybridization probe assays.

12 Claims, 6 Drawing Sheets

RECOMBINANT SIGMA NS PROTEIN

FIELD OF THE INVENTION

This invention relates to the synthesis by application of recombinant DNA technology of recombinant reovirus nonstructural protein sigma NS and its use as a non-specific binding agent for single stranded (ss) RNA's. This property of sigma NS protein can be employed when it is used as a reagent in protecting unstable RNA during extraction processes and more significantly as a reagent for the concentration of (ss) RNA samples for use in hybridization probe assays.

BACKGROUND OF THE INVENTION

The reovirus genome consists of 10 segments of double-stranded (ds) RNA. The segments are transcribed by virus-associated RNA polymerase to form capped m RNAs which also function as templates for a putative replicase in virus-infected cells. Each ds RNA segment codes for at least one protein. Two of these, $\mu_{NS}$, and $\sigma_{NS}$, encoded by genomic segments M3 and S3, respectively, are found only in infected cells. While the function of these two nonstructural proteins is unknown, there is some evidence to suggest that $\sigma_{NS}$ may act in the selection and condensation of the 10 different single-stranded (ss) RNAs into precursor subviral particles in preparation for ds RNA synthesis.

It is thus known in the art that $\sigma_{NS}$ has the capacity to bind ss RNAs as part of the putative viral replication system in infected cells. See in this regard Huismans and Joklik, Virology 70, 411–424 (1976). In addition, virus-specific particles sedimenting at 13-19S which are composed solely of $\sigma_{NS}$ were found to protect 20–40 nucleotide RNA fragments of reovirus mRNAs, including 3'termini, from nuclease digestion. See Stamatos and Gomatos, Proc. Natl. Acad. Sci. U.S.A. 79, 3457–3461 (1982).

The cloning of the reovirus genomic segment encoding $\sigma_{NS}$ and its sequencing has been described. See Imai et al., Proc. Natl. Acad. Sci. U.S.A. 80, 373–377 (1983) and Richardson and Furuichi, Nuc. Acids Res. 11, 6399–6408 (1983).

However, in the absence of a recombinant DNA system capable of expressing the desired $\sigma_{NS}$ protein it has not heretofore been possible to produce enough of the protein to fully explore the biological properties of this compound nor was it possible to determine whether the non-specific binding property of (ss) RNAs was retained by a recombinantly produced analog of this protein.

BRIEF DESCRIPTION OF THE INVENTION

Figure 1:
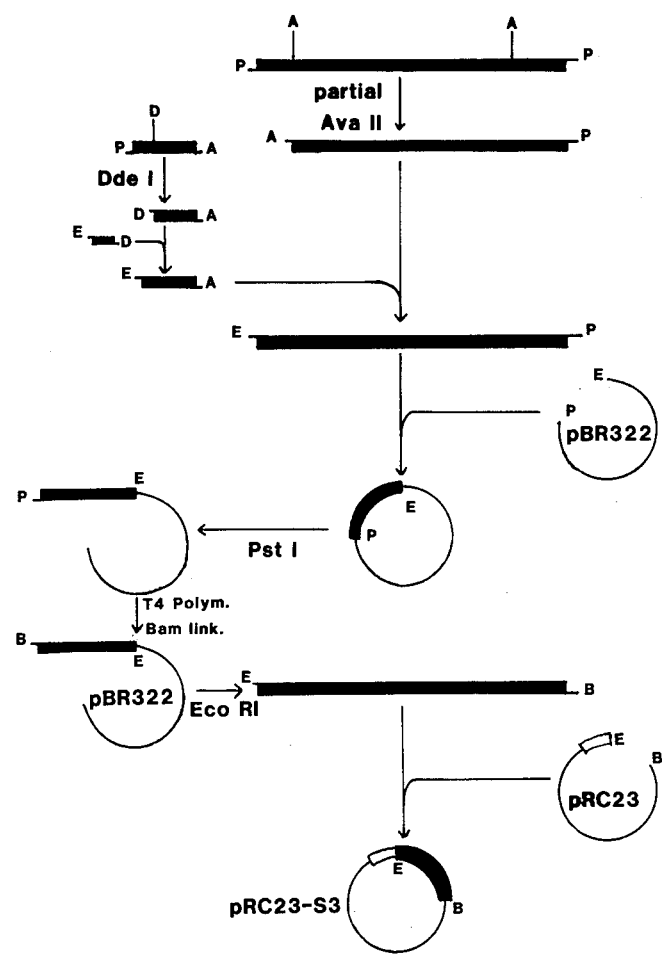
FIG. 1 shows an outline of the construction of plasmid pRC23-S3.

The present invention relates to the genetic engineering of the reovirus genomic segment coding $\sigma_{NS}$ to provide and to insert the coding region for $\sigma_{NS}$ into an expression plasmid, transforming a suitable microbial host organism with such resulting recombinant expression plasmid, fermenting such transformed microbial host organisms under conditions which favor expression of such plasmid thereby producing recombinant $\sigma_{NS}$ in such transformed microbial host organisms, purifying the so produced recombinant $\sigma_{Ns}$ free from microbial protein and employing such recombinant $\sigma_{NS}$ in the stabilization of ss RNAs and for the concentration of (ss) RNA samples for use in hybridization probe assays, preferably supported by covalent attachment to a suitable solid support matrix. As used herein the term "reovirus" is meant to include all three Reovirus serotypes designated Types 1, 2 and 3. Type 3 represents a preferred embodiment for use in the present invention.

A wide variety of known host-expression plasmid combinations may be employed in the practice of the present invention, such as, for example, plasmids from E. coli including Col El, pCR, pBR 322 and their derivatives, wider host range plasmids, e.g. RP4, phage DNA, e.g. the numerous derivatives of phage lambda e.g. NM 989 and vectors derived from combination of plasmids and phage DNAs such as plasmids which have been modified to employ phage DNA or other expression central sequences or yeast plasmids such as the $2\mu$ plasmid or derivatives thereof.

Useful hosts may include bacterial hosts such E. coli RRl, E. coli W 3110, E. coli HB 101, E. coli X 1776, E. coli X 2282, E. coli MRCl and strains of Pseudomonas, Bacillus subtilis, Bacillus stearothermophilus and many other bacilli, yeasts and other fungi hosts. It is also within the skill of the art to employ as recombinant hosts mammalian, insect or plant cells in culture. It is to be understood that not all host/vector combinations may be equally efficient for purposes of the present invention, a preferred recombinant host/vector system comprises the pRC23 expression plasmid containing the lambda $P_L$ promoter and a consensus Shine/Dalgarno ribosomal binding site and E. coli strain $RR_1$ host. In a further preferred embodiment of the invention pRC23 was propagated in the presence of the low-copy number compatible plasmid pRK248 cIts which carries the gene for a temperature-sensitive lambda cI repressor.

The known expression plasmid pRC23, (see Lacal et al, Proc. Natl. Acad. Sci. U.S.A. 81, 5305–5309 (1984)) a derivative of pBR322, was used to produce the reovirus nonstructural protein $\sigma_{NS}$ in *E. coli*. Expression of heterologous genes in pRC23 is driven by the phage lambda $P_L$ promoter. The plasmid was designed to express inserted genes utilizing their own initiating AUG codons, thus allowing the production of protein with a primary amino acid sequence identical to that of the authentic polypeptide. The $P_L$ promoter is under the control of the temperature-sensitive cI repressor encoded by the compatible plasmid pRK248cIts as described by Bernard and Helinski, Methods Enzymol. 68, 482–492 (1979). Hence, expression of the heterologous gene is repressed during cell growth at 30° C. and induced by shifting cells to 42° C.

The recombinant plasmid pRC23-S₃ was constructed following the strategy outlined below. Essentially, a cloned cDNA copy of reovirus genomic segment S₃ (encoding $\sigma_{NS}$) was modified by replacing the 5' non-coding region with an EcoRI cohesive end. This was accomplished by making use of a conveniently located DdeI site and a pair of synthetic complementary deoxyoligonucleotides. To enable correct insertion into pRC23, a BamHI site was added to the 3' end. Ligation to EcoRI/BamHI digested pRC23 resulted in the initiating AUG for $\sigma_{NS}$ being located immediately downstream of the consensus ribosomal binding site engineered into pRC23 as described by Lacal et al, supra.

The strategy employed is outlined in FIG. 1. Initially, a cloned cDNA copy of reovirus type 3 genomic segment S3 derived as described by Imai et al. supra was partially digested with AvaII. After polyacrylamide gel fractionation the purified fragment representing the 5' end of the S3 mRNA (147 bp, including GC tail), was further digested with DdeI, which cut 10 bases downstream of the initiating AUG triplet. Restoration of these bases to the coding region, and the addition of an EcoRI cohesive end, was achieved by ligation to a pair of synthetic complementary deoxyoligonucleotides, prepared by procedures known in the art. See Beaucage and Caruthers, Tetrahydron Lett. 22, 1859–1862 (1981) and Matteuci and Caruthers J. Amer. Chem. Soc. 103, 3185–3191 (1981). Following further polyacrylamide gel purification, the fragment containing the modified 5' end (now with an EcoRI site immediately upstream of the initiating AUG codon) was ligated back to the fragment representing the 3' end of the S3 mRNA (1,110 bp, including CG tail), and then the reconstructed S3 gene was subcloned into pBR322 at the EcoRI/PstI sites. Following PstI digestion, T4 DNA polymerase was used to blunt end the PstI site, BamHI linkers added and the resulting EcoRI/BamHI fragment put into pRC23 at the EcoRI/BamHI sites. This expression plasmid was designated pRC23-S3. It is, of course, well known in the art to substitute other linkers specifically designed to provide other restriction sites for insertion into any derived plasmid. All ligations, restriction enzyme digestions and bacterial transformations were carried out using standard conditions essentially as described by Maniatis et al, Molecular Cloning: A laboratory manual. Cold Spring Harbor Laboratory, Cold Spring Harbor, N.Y. (1982).

*E. coli* RRI (pRK248cIts) cells containing the pRC23-S3 expression plasmid were grown overnight at 30° C. in L-broth containing ampicillin (100 μg/ml) and tetracycline (15 μg/ml). These cultures were used to inoculate M9 minimal medium containing ampicillin at 100 μg/ml and supplemented with either proline (100 μl/ml) and leucine (50 μg/ml), or Casamino acids (CAA). Cultures were grown at 30° C. to the early logarithmic phase (OD₆₀₀ 0.2–0.3), divided in half and either maintained at 30° C. or transferred to a water bath at 42° C. Recombinant $\sigma_{NS}(r\sigma_{NS})$ synthesis was detected by pulse-labeling with [³⁵S]-methionine (15–16μCi per 150 μl of culture, 1400 ci/mmole) in M9 minimal medium containing proline and leucine. Synthesis could also be detected by Coomassie Brilliant Blue staining if cultures were grown in M9 minimal medium supplemented with CAA. Cell samples (usually 150 μl) were pelleted, dissolved in sample buffer and electrophoresed on either 10% or 12.5% SDS-polyacrylamide gels according to Laemmli, Nature (London) 227, 680–685 (1970).

RRI (pRK248cIts) cells containing pRC23-S3 expression plasmid were grown at 30° C. in M9 minimal medium supplemented with CAA to an OD₆₀₀ of 0.2–0.3. Cultures were transferred to 42° C. and cells were collected by centrifugation (Sorval RC3, 3500 rpm, 20 min) 3 hr later. Cell pellets were washed with 25 mM Tris, pH 7.5, 5 mM EDTA, repelleted and stored at −20° C. Cells were lysed by resuspension in lysis buffer [25 mM Tris, pH 7.5, 1 mM EDTA, 0.15 M NaCl, 1 mM DTT, 1 mM phenylmethylsulphonylfloride (pmsf), 5% glycerol and lysozyme at 0.2 mg/ml] using at least 70 ml per 250 ml of original culture. Chromosomal DNA and cell debris were pelleted by centrifugation at 17,000 rpm for 1 hr in an SW27 rotor. The supernatant was subjected to centrifugation (24,000 rpm, 6 hr, SW27 rotor) onto a 40% (W/V) sucrose cushion. The pellet, containing predominantly $r\sigma_{NS}$, was resuspended in lysis buffer (without lysozyme), made 0.8M with respect to NaCl and centrifuged at 35,000 rpm for 5 hr in an SW41 rotor. The salt concentration of the supernatant, containing $r\sigma_{NS}$, was reduced to less than 25 mM by buffer exchange with TEM buffer (25 mM Tris, pH 7.5, 1 mM 2-mercapto-ethanol) in an Amicon ultrafiltration cell (Amicon Corp., Danvers, MA; YM10 membrane). The supernatant was then applied to a poly(A)-agarose column (Pharmacia, AG-poly(A) type 6 column size 0.6 cm×3 cm), washed extensively with 0.1M NaCl-TEM buffer followed by 0.2M NaCl-TEM, and the bound $r\sigma_{NS}$ was eluted with 0.5M NaCl-TEM. The eluted fraction, after buffer exchange (to 25 mM Tris, pH 7.5, 1 mM EDTA, 1 mM DTT, 30% glycerol) and concentration in the Amicon ultrafiltration cell, was used in all nucleic acid binding experiments.

Figure 2:
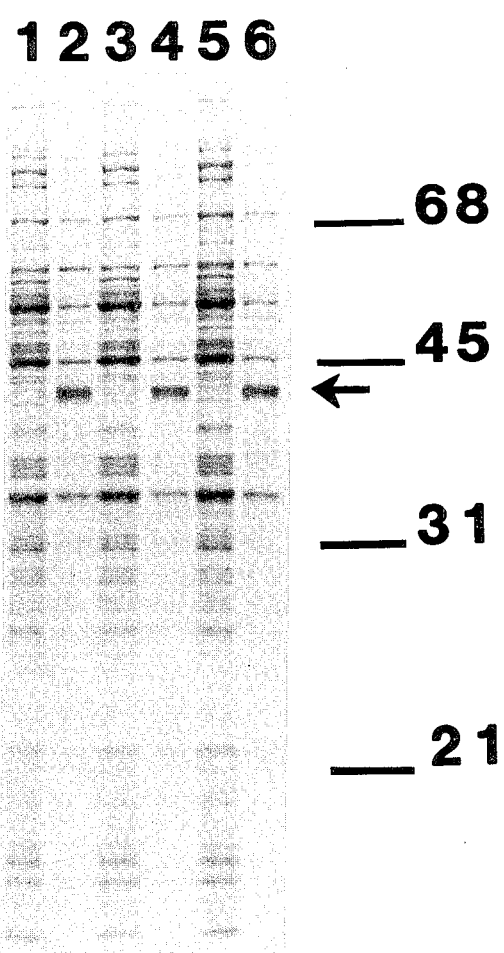
FIG. 2 shows an autoradiogram of an SDS polyacrylamide gel electrophoretic analysis of $^{35}$S-methionine-labeled proteins made by untransformed E. coli bacteria(lanes 1, 3 and 5) and bacteria containing plasmid pRC23-S3 (lanes 2,4 and 6), The numbers to the right show the positions of molecular weight marker proteins in Kdaltons. The arrow shows the position of $\sigma_{NS}$ band.
Figure 3:
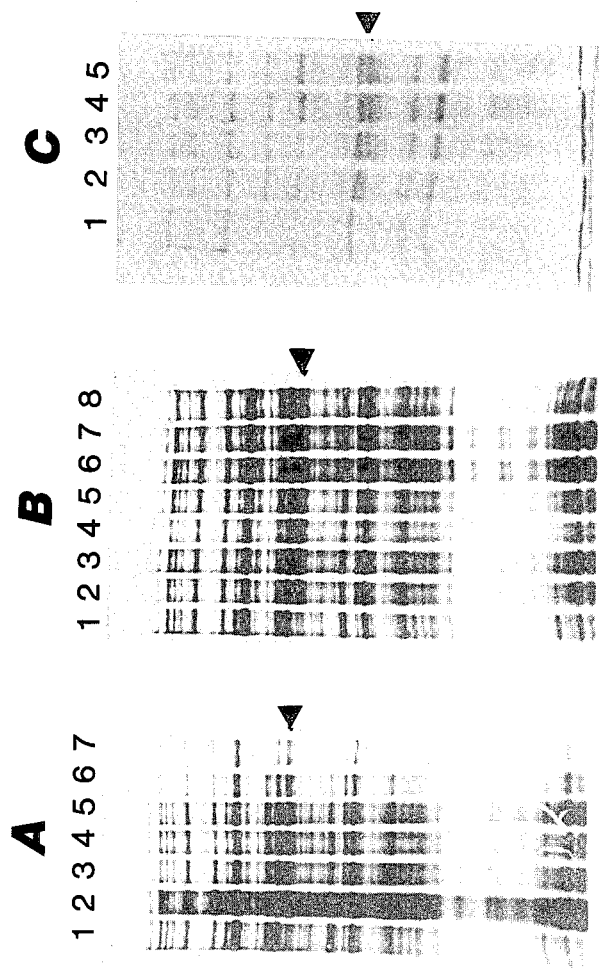
FIG. 3 shows in panels A and B autoradiograms of SDS polyacrylamide gel electrophoretic analyses of $^{35}$S-methionine labeled proteins made by reovirus-infected cells at various times after inducing protein synthesis at 42° C. (panel A) and at various times after chasing labeled cells with cold methionine at 42° C. (panel B). Panel C shows a Coomassie Blue stained SDS gel analysis of proteins made by transformed E. Coli at various times after the induction of protein synthesis at 42° C. The positions of the $\sigma_{NS}$ bands are shown by arrows.

Synthesis of $\sigma_{NS}$ in RR1 (pRK248cIts) cells transformed with pRC23-S3 was detected by pulse-labeling with [³⁵S]-methionine followed by SDS-polyacrylamide gel electrophoresis and autoradiography (FIG. 2). In the three transformants examined, incubation at 42° C. resulted in the synthesis of a protein of approximate molecular weight 41,000 (lanes 2, 4 and 6). The induced protein comigrated with $\sigma_{NS}$ synthesized in reovirus infected L-cells (see FIG. 3) and was designated here recombinant $\sigma_{NS}$ ($r\sigma_{NS}$). Recombinant $\sigma_{NS}$ was detected within 5 min of shifting cultures to 42° C. and was still being synthesized 6 hr after induction (FIG. 3A). In a pulse-chase experiment, $r\sigma_{NS}$ labeled 30 min after cultures were transferred to 42° C. and then chased with cold methionine proved to be quite stable, still being detectable 6 hr after labeling (FIG. 3B). As might be expected from these results, the presence of r$\sigma_{NS}$ in *E. Coli* extracts could be detected by staining SDS-polyacrylamide gels with Coomassie Brilliant Blue (FIG. 3C). Maximum accumulation of r$\sigma_{NS}$ occurred by 3 hr post-induction, at which time r$\sigma_{NS}$ constituted 6–7% of total cellular protein. This time was chosen for large scale production of r$\sigma_{NS}$.

Figure 4:
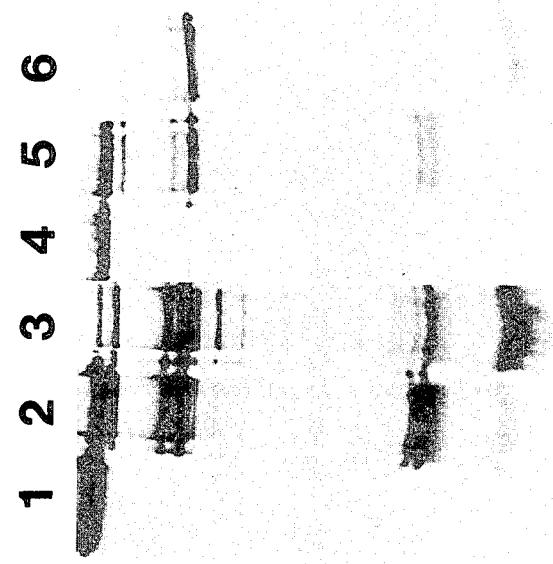
FIG. 4 shows a gel electrophoretic comparison of $\sigma_{NS}$ protein produced in transformed E. coli and in reovirusinfected L-cells, following partial digestion of the protein with S. aureus V8 protease.
Figure 5:
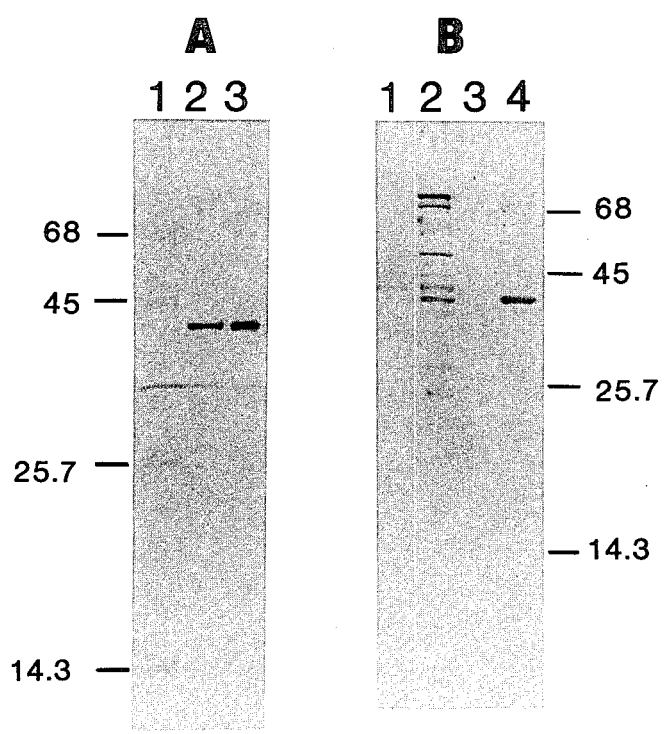
FIG. 5 shows immunoblot analysis of $\sigma_{NS}$ protein produced in reovirus infected cells (panel A) and in transformed E. coli (panel B). Molecular weight marker positions in kdaltons are indicated by numbers. The position of $\sigma_{NS}$ is shown by arrows.

The authenticity of r$\sigma_{NS}$ produced in *E. coli* cells was examined in two ways; by (1) partial proteolytic digestions using *S. aureus* V8 protease; and (2) reactivity with antibody in immunoblots. V8 protease digestions of r$\sigma_{NS}$ and authentic $\sigma_{NS}$ obtained from reovirus-infected L-cells indicated that the two proteins were, by this criterion, identical (FIG. 4). In immunoblots, rabbit antibodies raised against r$\sigma_{NS}$ reacted with authentic $\sigma_{NS}$ synthesized in infected L-cells (FIG. 5A). Also, rabbit antibodies raised against reovirus infected cells (and, hence, recognizing most reovirus specific proteins) reacted with r$\sigma_{NS}$ (FIG. 5B). These results provided further evidence that r$\sigma_{NS}$ was similar, if not identical, to the authentic $\sigma_{NS}$ produced in virus-infected cells.

Figure 6:
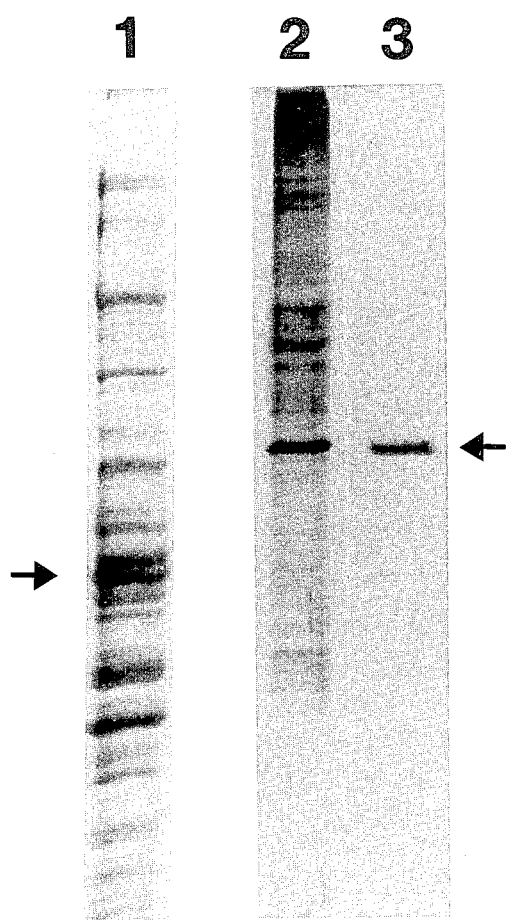
FIG. 6 shows the silver stained SDS polyacrylamide gel electrophoretic analysis of a total extract from transformed E. coli (lane 1), a high salt extract of an insoluble fraction frm the total extract (lane 2), and a fraction from the high salt extract purified by poly(A)agarose column chromatography. The position of $\sigma_{NS}$ protein in the gels is shown by arrows.

The r$\sigma_{NS}$ produced in transformed recombinant cells as described above can be purified as follows. Cells containing the expression plasmid pRC23-S3 were grown and induced in M9 minimal medium containing CAA as described above. The supernatant (lane 1, FIG. 6) was subjected to further centrifugation at 24,000 rpm to pellet r$\sigma_{NS}$. Recombinant $\sigma_{NS}$ was solubilized by resuspension in high salt buffer and insoluble contaminants were pelleted by centrifugation at 35,000 rpm. The supernatant (lane 2, FIG. 6), after buffer exchange to lower the salt concentration, was subjected to poly-(A)-agarose column chromatography as described above. Recombinant $\sigma_{NS}$ was purified by this procedure to virtual homogeneity as judged by SDS-polyacrylamide gel electrophoresis and silver staining (lane 3, FIG. 6). This fraction was used for subsequent binding experiments.

Initially the ability of r$\sigma_{NS}$ to bind reovirus mRNAs that were methylated and capped was compared to its ability to bind uncapped mRNAs. Accordingly, [$^{32}$P]-labeled reovirus (ss) RNAs synthesized in vitro in either the presence or absence of S-adenosyl methionine were mixed with purified r$\sigma_{NS}$ and the binding capabilities were determined. Recombinant $\sigma_{NS}$ bound both mRNAs with equal efficiency, with greater than 90% of the [$^{32}$P]-labeled input mRNAs being retained on the filter (Table 1), suggesting that 5'-cap structure was not necessary for binding. A similarly purified fraction from non-induced *E. coli* cultures did not bind either of the mRNAs. Neither did the fraction from induced cultures that eluted with low salt from the poly(A)-agarose column, even though at least 50% of r$\sigma_{NS}$ loaded on the column was found in this fraction (Table 1). This result indicated that not all r$\sigma_{NS}$ proteins were capable of binding (ss) RNAs, a characteristic also reported for $\sigma_{NS}$ obtained from reovirus-infected L-cells. It should be pointed out that native $\sigma_{NS}$ protein was essential for binding, as boiling r$\sigma_{NS}$ for 5 minutes drastically reduced binding activity (by 90%, data not included). Hence, a non-specific aggregation of r$\sigma_{NS}$ and reovirus mRNAs appears to be ruled out.

The specificity of r$\sigma_{NS}$ binding was examined next. Recombinant $\sigma_{NS}$ was mixed, as described above, with either reovirus (ss) RNA, cytoplasmic polyhedrosis virus (CPV) (ss) RNA, reovirus dsRNA or CPV dsRNA. Neither of the [$^{32}$P]-labeled dsRNAs were retained on the filter (Table 2), demonstrating that r$\sigma_{NS}$, like authentic $\sigma_{NS}$ from infected L-cells, had low or no affinity for dsRNAs. Both (ss) RNAs were bound, apparently with equal efficiency (Table 2). This study was extended by examining the ability of r$\sigma_{NS}$ to bind yeast rRNA, yeast tRNA and native and denatured dsDNA (a pBR322 fragment). While the overall percentage of input nucleic acid retained on filters was less than that in previous experiments, the results were the same (Table 2). Thus, the three (ss) RNAs (reovirus, CPV and yeast rRNA) were bound to approximately the same extent whereas the two (ds)RNAs (reovirus and CPV) were not bound at all. While the dsDNA was not retained on filters, consistent with the previously characterized $\sigma_{NS}$ from infected L-cells, denatured dsDNA was retained, although not to the same extent as (ss) RNAs. Retention of yeast tRNA, which has extensive secondary structure, was low (Table 2).

The number of available binding sites was estimated in competition experiments using unlabeled reovirus (ss) RNAs. For approximately 130 ng of r$\sigma_{NS}$, 10–15 ng of competing (ss) RNA was sufficient to cause a significant reduction in the binding of [$^{32}$P]-labeled reovirus (ss) RNA (data not shown). From this it could be estimated that the molar ratio of r$\sigma_{NS}$ to bound (ss) RNA was approximately 150 to 1. This was close to that estimated for $\sigma_{NS}$ from infected L-cells by Stomatos and Gomatos supra.

In a preliminary experiment it was noticed that the capacity of r$\sigma_{NS}$ to bind (ss) RNAs was abolished if all four ribonucleotides were included in the reaction mixture. The ability of each of the four ribonucleotides (ATP, CTP, GTP, and UTP) to inhibit binding was then examined. GTP alone proved able to reduce binding to the extent observed when all four ribonucleotides were included (Table 3). With the amount of r$\sigma_{NS}$ used in these experiments (130 ng per reaction) GTP inhibition was evident between 0.5 mM and 1 mM (Table 3). The other three ribonucleotides caused little interference with binding even at concentrations of 10 mM (Table 3). This was an important observation for developing $\sigma_{NS}$ as a concentrator of (ss) RNA in test samples to be used in hybridization probe assays. The ability to reversibly bind the (ss) RNA to $\sigma_{NS}$ protein gives the tester the option of hybridizing the bound (ss) RNA with the probe or if the bound (ss) RNA does not hybridize with the probe due to blockage of the hybridization site by the binding of the $\sigma_{NS}$ protein, then the concentrated sample (ss) RNA can be eluted from the protein complex by use of a solution of GTP or salt. The isolated (ss) RNA can then be treated with the hybridization probe in a conventional manner. Obviously since the binding of the $\sigma_{NS}$ protein with the (ss) RNA is non-specific, the specificity of the assay is fully determined by the specificity of the hybridization probe for the desired RNA being assayed.

While it is possible to utilize $\sigma_{NS}$ in solution to treat (ss) RNA to effect stabilization or even to effect concentration of the (ss) RNA by complexing with $\sigma_{NS}$ protein followed by isolation of the complex such as by sucrose gradient centrifugation the preferred embodiment of the invention is to immobilize the $\sigma_{NS}$ protein on a solid matrix and pass the (ss) RNA sample solution through the immobilized $\sigma_{NS}$ containing matrix. Suitable matrices for this purpose are well known in the art and include Sepharose or Agarose beads treated in a manner known per se to allow direct covalent coupling with protein such as, for example, with cyanogen bromide. Other supports for this purpose include cellulose, particularly nitrocellulose preferably in the form of filters, silica derivatized to react with protein functional groups i.e., —COOH, —OH, —NH$_2$ or —SH groups, polymeric microtiter plates and test tubes and the like. Covalent coupling can be achieved using reagents which are conventionally used to react with proteins such as carbodiimides e.g. dicylcohexylcarbodiimide to provide direct coupling to the support or by using bifunctional linking groups such as glutaraldehyde to provide coupling through a linker.

The conditions employed are those well known in the art to effect the reaction between the specific solid matrix employed and the $\sigma_{NS}$ protein depending on the choice of coupling reagent and, where employed, the bifunctional linking group.

It is also possible to bind protein to solid supports, particularly polymeric multititer plates, by utilizing absorption rather than covalent bonding. In such embodiments dilute solutions of the $\sigma_{NS}$ protein in buffer at a pH in the range of about 7-8 are placed in the wells and allowed to dry overnight under a nitrogen stream at 37° C. The resulting plates can be used in the same manner as those prepared using the covalent coupling procedures described above.

The hybridization assay can be carried out conveniently by passing the test solution containing the (ss) RNA over the solid supported $\sigma_{NS}$ protein if a bead matrix is used such as for example in the form of a chromatographic column. Alternatively, the $\sigma_{NS}$ protein can be used to coat a microtiter plate or the inside of a test tube in a manner known per se. The test sample is then added to the plate or tube and any (ss) RNA in the sample is allowed an opportunity to complex with the bound $\sigma_{NS}$ protein and then the sample solution is removed and the plate or tube washed. Similarly if a nitrocellulose filter supported $\sigma_{NS}$ protein is used, then the test sample is passed through the filter one or more times to allow binding to take place.

The source of test sample can be tissue extracts, body fluids, cell lysates and the like. Assays can be carried out for determining the presence of abnormal genes to detect genetic abnormalities, to detect active oncogenes to determine risk of neoplastic disease states, to detect parasitic diseases to detect infectious diseases or for any other purposes to which hybridization probe assays are run in the art.

The hybridization probe is usually a strand of natural or synthetic DNA or RNA of known sequence which is complementary to at least a portion of the (ss) RNA which is being assayed. The probe carries a detectable signal ligand to allow detection of the hybridized complex after excess non-reacted probe is washed away. Suitable signal ligands for this purpose are known to the art and many are articles of commerce. Such ligands include radioactive isotopes such as $^{125}I$, $^{32}P$, $^{3}H$ $^{35}S$ and the like, such ligands can be detected in a conventional manner in a scintillation counter; chromophores which can be detected by spectrographic analysis; fluorophors which can be detected by a fluorimeter, enzyme labels such as horseradish peroxidase which can be detected by changes in a chromogenic substrate; and luminescent ligands such as luminol and isoluminol and bioluminescent ligands, such as aequorin which can be detected by a luminometer or any conventional photon counting device.

As pointed out previously the reaction between the hybridization probe and the (ss) RNA can be carried out directly on the solid support complexed material if the interaction with the $\sigma_{NS}$ protein does not block the hybridization binding site. On the other hand if it is not possible to carry out such a direct assay then the complexed (ss) RNA is removed from the solid supported $\sigma_{NS}$ by treating with a solution of GTP.

The assays are usually read in a (+)/(−) configuration, that is, the indicated RNA sequence is present as seen by the observation of the detectable signal in the monitoring equipment discussed above. However, in appropriate circumstances it is possible to use known concentrations of the test (ss) RNA in the assay procedure and plotting the values of the signals observed to provide a standard curve which would allow one if the sensitivity of the assay is appropriate, to quantitate the unknown (ss) RNA.

In a further aspect of the invention a test kit is provided which provides a convenient means for carrying out a hybridization probe assay with concentration of the test sample (ss) RNA. Such test kit, in a preferred embodiment, comprises a first container containing sufficient $\sigma_{NS}$ protein covalently bound to a solid matrix to carry out multiple assays. As a general rule of thumb the molar ratio of $\sigma_{NS}$ to bound (ss) RNA is approximately 150 to 1 and thus the amount of matrix $\sigma_{NS}$ protein to be used for any single assay determination can be readily determined. The solid matrix can be beads, microtiter plates, tubes or filter paper as indicated previously.

The second container in the kit will contain sufficient hybridization probe reagent bearing a detectable signal ligand to carry out multiple assays. Multiple containers of such reagents with different probes may be provided to allow assays to be carried out against multiple products.

Optionally, the kit may also contain a container of GTP or salt solution, preferably at a concentration of between about 0.5 mM to 1.0 mM, to allow the complexed (ss) RNA to be eluted free of the $\sigma_{NS}$ protein before the assay is carried out where the complex interferes with hybridization. Again sufficient solution may be provided to allow multiple assays to be carried out.

In a further embodiment of the invention, the $\sigma_{NS}$ protein may be provided covalently bound to polymeric microbeads pre-packed in disposable columns allowing the user to simply pass the test solution through the column followed by a wash and then passing the hybridization probe reagent through the column to provide a quick, simple, sensitive and efficient assay system. If the sample contained any specific (ss) RNA, the probe reagent would hybridize to it and the complex would be detected by the label on the probe reagents.

TABLE 1

| Binding of reovirus ssRNAs by r$\sigma_{NS}$[a] | | | | |
|---|---|---|---|---|
| | | 42° induced cultures poly(A)-agarose eluted[b] | | 30° non-induced cultures poly(A)-agarose eluted[b] |
| | | high salt fraction | low salt fraction | high salt fraction |
| % of [$^{32}$P]-labeled reovirus ssRNAs retained on nitrocellulose membrane | +SAM | 94 | 0 | 0 |
| | −SAM | 100 | 1 | 0 |

[a]Conditions used as described in Materials and Methods.
[b]Obtained as described in Materials and Methods.

TABLE 2

Specificity of nucleic acid binding to $r\sigma_{NS}{}^a$

| | | reovirus ssRNA | CPV ssRNA | reovirus dsRNA | CPV dsRNA | rRNA | tRNA | denatured dsDNA[b] | dsDNA |
|---|---|---|---|---|---|---|---|---|---|
| % of [$^{32}$P]-labeled nucleic acid retained on nitrocellulose membrane | EXP. 1 | 78 | 87 | 1 | 2 | | | | |
| | EXP. 2 | 50 | 79 | 2 | 2 | 51 | 15 | 27 | 1 |

[a]Conditions used as described in Materials and Methods.
[b]dsDNA was denatured by boiling in TE buffer for 5 min and quick chilling in ice H$_2$O.

TABLE 3

Inhibition of binding of reovirus ssRNA to $r\sigma_{NS}$ by GTP[a]

| | | Ribonucleotide | | | | | |
|---|---|---|---|---|---|---|---|
| % of [$^{32}$P]-labeled reovirus ssRNA retained on nitrocellulose membrane[b] | EXP. 1 | None | ATP 2 mM | CTP 2 mM | GTP 2 mM | UTP 2 mM | Mixture of ATP, CTP, GTP, UTP 2 mM each |
| | | 100 | 61 | 58 | 5 | 59 | 5 |
| | EXP. 2 | None | | GTP | | | ATP / CTP / UTP |
| | | | 0.1 mM | 0.5 mM | 1 mM | 2 mM | 10 mM / 10 mM / 10 mM |
| | | 100 | 93 | 95 | 29 | 15 | 0 / 95 / 81 / 68 |

[a]Conditions used as described in Materials and Methods.
[b]Expressed as percentage of control.

What is claimed is:

1. A $\sigma_{NS}$ composition comprising $\sigma_{NS}$ protein characterized by freedom from other proteins, as determined by SDS-polyacrylamide gel electrophoresis, covalently bound to a solid support matrix.

2. The composition of claim 1 wherein said $\sigma_{NS}$ protein is recombinant $\sigma_{NS}$ protein.

3. The composition of claim 1 wherein said solid support matrix is beads, microtiter plates, test tubes or nitrocellulose filter paper.

4. The composition of claim 3 wherein said solid support matrix is beads which are packed within disposable columns.

5. A method for carrying out a hybridization probe assay for a specific (ss) RNA, which method comprises:
   (a) treating a test sample solution with $\sigma_{NS}$ protein to bind (ss) RNA contained in the test sample non-specifically to the $\sigma_{NS}$ protein to produce a (ss)RNA-$\sigma_{NS}$ complex;
   (b) separating the (ss) RNA-$\sigma_{NS}$ complex from the remainder of the test sample to concentrate the bound (ss) RNA;
   (c) treating the separated (ss) RNA-$\sigma_{NS}$ complex with a hybridization probe reagent containing a detectable signal ligand, which reagent comprises an RNA or DNA segment complementary to the sequence of the specific (ss) RNA to be assayed;
   (d) separating unbound hybridization reagent; and
   (e) testing the (ss) RNA-$\sigma_{NS}$ complex for the presence of detectable label, which label indicates the presence of specific (ss) RNA.

6. The method of claim 5 in which the $\sigma_{NS}$ protein is provided covalently bound to a solid support matrix.

7. The method of claim 5 in which the $\sigma_{NS}$ protein is recombinant $\sigma_{NS}$ protein.

8. The method of claim 5 in which the detectable signal ligand is a radioisotope, a chromophore, a fluorophor or an enzyme.

9. A method for carrying out a hybridization probe assay for a specific (ss) RNA, which method comprises:
   (a) treating a test sample solution with $\sigma_{NS}$ protein to bind (ss) RNA contained in the test sample non-specifically to the $\sigma_{NS}$ protein to produce a (ss) RNA-$\sigma_{NS}$ complex;
   separating the (ss) RNA-$\sigma_{NS}$ complex from the remainder of the test sample to concentrate the bound (ss) RNA;
   (c) treating the separated (ss) RNA-$\sigma_{NS}$ complex with a GTP or salt solution to dissociate the complex;
   (d) immobilizing the dissociated (ss) RNA on a filter;
   (e) treating the immobilized (ss) RNA with a hybridization probe reagent containing a detectable signal ligand, which reagent comprises an RNA or DNA segment complementary to the sequence of the specific (ss) RNA to be assayed;
   (f) separating unbound hybridization reagent from the immobilized (ss) RNA; and
   (g) testing the immobilized (ss) RNA for the presence of detectable label, which label indicates the presence of specific (ss) RNA.

10. The method of claim 9 in which the $\sigma_{NS}$ protein is provided covalently bound to a solid support matrix.

11. The method of claim 9 in which the $\sigma_{NS}$ protein is recombinant $\sigma_{NS}$ protein.

12. The method of claim 9 in which the detectable signal ligand is a radioisotope, a chromophore, a fluorophor or an enzyme.

* * * * *